(12) United States Patent
Nielsen

(10) Patent No.: US 8,870,943 B2
(45) Date of Patent: Oct. 28, 2014

(54) STENT STRUCTURE FOR IMPLANTABLE MEDICAL DEVICE

(71) Applicant: Arne Molgaard Nielsen, Copenhagen (DK)

(72) Inventor: Arne Molgaard Nielsen, Copenhagen (DK)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/787,000

(22) Filed: Mar. 6, 2013

(65) Prior Publication Data
US 2014/0074221 A1    Mar. 13, 2014

(30) Foreign Application Priority Data

Sep. 12, 2012 (EP) ................................. 12275140
Sep. 12, 2012 (GB) ................................. 1216279.8

(51) Int. Cl.
*A61F 2/86* (2013.01)
*A61F 2/89* (2013.01)
*A61F 2/90* (2013.01)

(52) U.S. Cl.
CPC ........... *A61F 2/89* (2013.01); *A61F 2250/0018* (2013.01); *A61F 2220/0016* (2013.01); *A61F 2210/0004* (2013.01); *A61F 2220/0075* (2013.01); *A61F 2250/001* (2013.01); *A61F 2/90* (2013.01); *A61F 2250/0082* (2013.01)
USPC ........................................ 623/1.16; 623/1.15

(58) Field of Classification Search
CPC     A61F 2/93; A61F 2002/826; A61F 2002/828
USPC ....................................... 623/1.15, 1.16, 1.18
See application file for complete search history.

(56) References Cited

U.S. PATENT DOCUMENTS

| | | | |
|---|---|---|---|
| 6,053,940 A | 4/2000 | Wijay | |
| 6,551,351 B2 * | 4/2003 | Smith et al. | ............... 623/1.16 |
| 2005/0228486 A1 | 10/2005 | Case et al. | |
| 2006/0004436 A1 | 1/2006 | Amarant et al. | |
| 2009/0005848 A1 | 1/2009 | Strauss et al. | |
| 2009/0157158 A1 * | 6/2009 | Ondracek et al. | ............... 623/1.2 |
| 2010/0249902 A1 | 9/2010 | Sakai et al. | |
| 2011/0166640 A1 | 7/2011 | Leewood et al. | |

OTHER PUBLICATIONS

Examination Report under Section 18(3) in related United Kingdom application No. GB1216279.8, mailing date Aug. 27, 2013.

* cited by examiner

*Primary Examiner* — David Isabella
*Assistant Examiner* — Dinah Baria
(74) *Attorney, Agent, or Firm* — Brinks Gilson & Lione

(57) ABSTRACT

A stent (30) is formed of a plurality of stent rings (24), each of which rings (24) is formed of a series of sprung sections (10) coupled to one another by flexible couplings (22). The flexible couplings (22) may be made of a biodegradable material. The flexible couplings (22) enable the stent (30) to expand to a smaller uncompressed diameter and then to expand further to a larger uncompressed diameter, by virtue of the flexible couplings (22) which allow the sprung sections to move from a partially overlapping configuration to a radially spaced configuration. The stent (30) can expand with expansion of a vessel, for example in a growing patient.

21 Claims, 4 Drawing Sheets

STENT STRUCTURE FOR IMPLANTABLE MEDICAL DEVICE

This application claims the benefit of the filing date of United Kingdom (GB) patent application number 1216279.8, filed Sep. 12, 2012, and European Patent Office (EP) patent application number 12275140, filed Sep. 12, 2012, both of which are hereby incorporated by reference herein.

TECHNICAL FIELD

The present invention relates to a stent structure for an implantable medical device.

BACKGROUND ART

Stents are widely used for a significant variety of endoluminal treatments of patients. They may be used by themselves or as part of another medical device, such as a stent graft, a vena cava filter, an occluder, and so on.

Stents need to be able to maintain a lumen open as well as to press against the lumen wall with sufficient force to hold the stent in place over long periods of time and often indefinitely. Balloon expandable stents will typically be expanded to a diameter slightly larger than the normal lumen diameter; whereas self-expanding stents are chosen to have a relaxed diameter which is greater than the normal diameter of the lumen, such that they maintain a constant opening pressure against the vessel walls.

There is a compromise between the pressure applied by a stent and the integrity of the vessel, in that too great a pressure can lead to damage to the vessel wall, whereas too low a pressure can lead to failure of the stent to hold the vessel sufficiently open and failure to anchor reliably to the vessel. Whilst in most instances this compromise can be adequately managed in a patient, difficulties arise in cases where the shape or dimensions of the lumen are not consistent over time. One such instance is in the case of a lumen which expands over time, such as in a growing child, and/or in the case of severe injury such as an aortic transection following accident. Thus, a stent or stented medical device implanted into the patient to effect a medical treatment at a given point in time may become too small, that is narrow, as the patient's lumens heal and/or otherwise grow with age. Such change in the patient's lumen may lead to consequential risk of loss of anchoring of the medical device in the lumen and possible migration through the patient's vasculature; in other circumstances artificial constriction of the vessel as a result of device ingrowth into the vessel wall, thereby preventing natural expansion of the vessel.

It is not practicable or ideal to use a large diameter stent given the potential risk of damage to the vessel wall while the vessel has a smaller natural diameter, and it is equally not practicable to try to constrict the diameter of the vessel over time. As a result, it is often necessary to contemplate removal of the stent or other medical device after widening of the vessel, which involves a second medical procedure and frequent investigations up to that point. Even so, such a medical procedure may be difficult or not possible due to ingrowth of the device.

It is possible, especially in a growing patient or following severe vessel damage due to accident for instance, that the implantation of the medical device need only be temporary as growth/healing itself or a change in the patient's lifestyle or medical condition obviates the further need for the function of the medical device.

It is not just in patients who may experience changing lumens that it may be desirable to remove the stent or other medical device after a treatment period. Once the medical condition has been successfully treated, it may be desirable to remove the device given that this will continue to apply unnatural forces to the vessel walls. However, as explained above, ingrowth of the device into the tissue of the vessel walls or movement thereof can make removal of the device difficult. For this purpose, bioresorbable or biodegradable medical devices have been proposed, in which at least a part of the device is made of materials which will degrade over time, either into the blood stream or into the vessel tissue.

It is, however, not a simple task to replace parts of a medical device with bioresorbable or biodegradable material since this can lead to a change in the performance characteristics of the device. For instance, a self-expanding stent has a given springiness and is thus able to apply a given expansion or opening force to a vessel, normally over a variety of vessel diameters and vessel shapes, which cannot be emulated by biodegradable or bioresorbable materials.

Examples of prior art stents and other medical devices can be found, for instance, in U.S. Pat. No. 6,053,940, US-2005/228,486, US-2006/0,004,436, US-2010/0,249,902 and US-2011/0,166,640.

DISCLOSURE OF THE INVENTION

The present invention seeks to provide an improved stent or other medical device.

According to an aspect of the present invention, there is provided a stent structure for an implantable medical device including a plurality of sprung sections, a plurality of flexible couplings each disposed between adjacent sprung sections so as to couple the sprung sections together into an annular shape, wherein the flexible couplings are substantially inextensible; said sprung sections being radially compressible from a rest configuration; wherein said structure has a first diameter when the sprung sections are compressed and a second diameter when the sprung sections are in said rest configuration, said flexible couplings allowing for expansion of said structure to a diameter greater than said second diameter.

The flexible couplings are advantageously non-sprung, that is they preferably do not produce any or only nominal restoring force when deformed or reconfigured. In practice, the flexible couplings allow the sprung sections to overlap one another in one configuration and to be spaced from one another in another configuration, the amount of overlap and spacing being delimited by the operable length of the flexible couplings.

This structure can provide a stent which is able to be radially compressed in a manner analogous to a conventional stent, by compression of sprung elements, which will then apply a conventional expansion force to the structure. The flexible couplings in practice will not affect the spring characteristics of the structure, which is therefore able to emulate a conventional stent structure. This is equally replicated as the stent expands from a radially contracted configuration up to its maximum diameter following its expansion. During this movement, the flexible couplings act to transfer force to the sprung sections, enabling them to apply their expansion forces in unison. The structure can, however, expand beyond its normal expanded diameter, by virtue of the flexible couplings, which can allow the structure to grow radially even once the sprung sections have attained their rest conditions, that is their fully expanded conditions. Such increase in the diameter of the structure does not cause the sprung sections to deform as the increase is accommodated by the flexible couplings, thereby without creating any contracting force.

In practice, the stent structure is preferably able to be endothealised into the walls of a patient's vessel. Even after such endothealisation, should the vessel change dimension, and/or shape, as may for instance occur in a growing patient, the stent can expand with the vessel without restricting this expansion.

In the preferred embodiment, the sprung sections and flexible couplings provide a discontinuous ring of spring material.

Advantageously, the flexible couplings are formed from a fibrous material, such as a thread.

Preferably, the flexible couplings are made of a biodegradable material. Such material can thus cause the stent structure to separate over time, resulting in a removal of the stent forces on the vessel and thus allowing the vessel to move naturally after time. This can be particularly useful in any medical condition where the medical device is only temporarily needed. The material may be such as to degrade over a number of weeks or months.

In the preferred embodiments, the sprung sections are made of a polymer, a metal or a metal alloy, such as a shape memory material, in particular Nitinol. The structure allows the use of sprung sections of conventional spring materials and which can thus behave in an analogous manner to conventional stent structures in terms of the expansion forces it will generate.

Typically, the sprung sections may have a curved form, preferably being V-shaped. Such a shape for the sprung sections, it has been found, provides reliable and optimum radial compressibility as well as substantially uniform opening force of the stent structure.

In an embodiment the sprung sections are arranged in a zigzag configuration.

Advantageously, the sprung sections are provided with at least one rounded coupling element for attachment to the flexible couplings. Rounded coupling elements are convenient for tying flexible couplings in the form of threads to the sprung sections, as well as avoiding any sharp ends or edges which could otherwise risk damaging the vessel walls.

According to another aspect of the present invention, there is provided an implantable medical device including a plurality of stent rings having a stent structure as taught herein, wherein the stent rings are coupled to one another to form a tubular structure.

The stent rings are preferably coupled together by tie elements between longitudinally adjacent sprung elements of adjacent stent rings, which tie elements may be flexible and may be biodegradable.

The implantable medical device may be stent, stent graft, vena cava filter, occlusion device or other implantable medical device.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Described below are embodiments in the form of a stent. The teachings herein are applicable to stents as well as to other medical devices which are stented, such as stent grafts, vena cava filters, occlusion devices, and so on.

The stented structure preferably has sprung sections made from a shape memory material but this is not essential. The teachings herein apply equally to other materials such as spring steel and other biocompatible materials.

Figure 1:
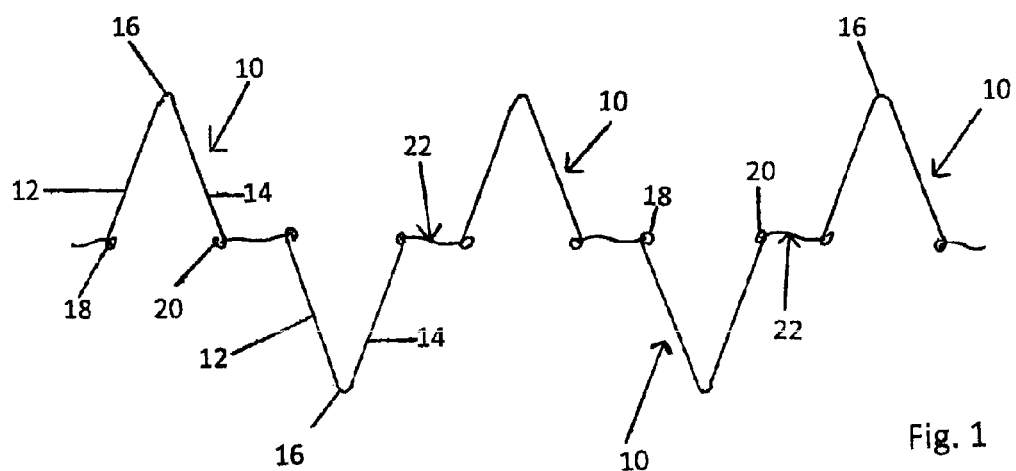
FIG. 1 is a schematic view of a part of an embodiment of stent structure.

Referring to FIG. 1, there is shown in flat form a part of a stent ring according to the preferred embodiment of the present invention. The structure includes a plurality of sprung sections 10 which in this embodiment are V-shaped, that is have first and second substantially straight arms 12, 14 joined integrally at an apex 16. The apex 16 is narrow in this embodiment, that is has a small radius of curvature.

The free ends of the arms 12, 14 are curved into annular coupling elements or rings 18,20.

The sprung sections 10 may typically be formed of wire, bent into the shape shown in FIG. 1, but may equally be cut to this shape, for example by laser cutting a metal sheet. Similarly, the annular coupling elements 18, 20 may also be laser cut into the metal of the sprung sections 10.

Although the sprung sections 10 may be planar, they may advantageously have a slight circumferential curvature such that the arms 12, 14 and rings 18, 20 follow the arc of a circle. Such curvature preferably follows the circumferential perimeter of the stent ring when in a relaxed condition. Such curvature can assist in the compression of the stent, as described below.

The sprung sections are preferably made from a shape memory material such as nickel titanium alloy (typically Nitinol) but could equally be made of another alloy or shape memory polymer, or from a spring material such as spring steel or cobalt chromium alloy.

Figure 2:
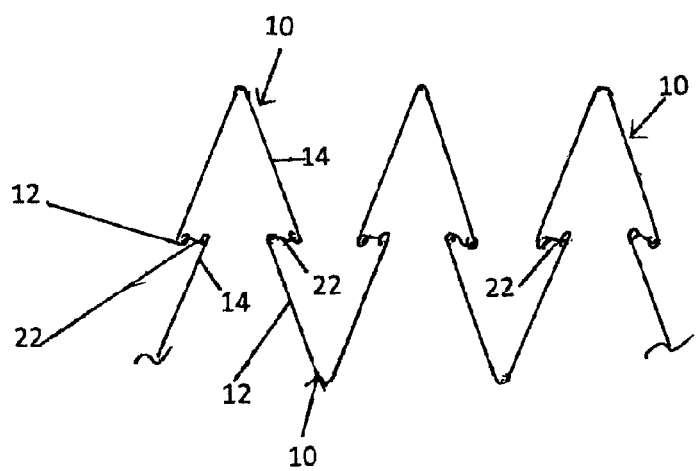
FIG. 2 is a perspective view of the stent structure of FIG. 1 with sprung sections thereof in an overlapping configuration.

It is preferred that the sprung sections 10 are arranged in a zigzag manner as shown in FIGS. 1 and 2, that is with adjacent sections 10 pointing in opposite directions. This provides good stability during compression and expansion of a stent ring formed by this structure. In other embodiments, though, the arrangement of the sprung sections 10 may be different and they may, for example, all point in the same direction or there may be a first stent ring having its sprung sections pointing in one direction and an adjacent stent ring having its sprung sections pointing in the opposite direction.

Adjacent sprung sections 10 are connected together by flexible couplings 22, which in the embodiment shown connect to the rings 18, 20 at the ends of the arms 12, 14. These flexible couplings may be made of flexible material, such as suture thread of the type used in implantable medical devices. However, they may also be made of relatively rigid material coupled to the arms 12, 14 by flexible or rotatable connections, for instance being in the form of metal tie bars which pivotably or rotatably couple to the rings 18, 20. As is explained below, the purpose of the couplings 22 is to allow adjacent coupled arms 14, 16 to move relative to one another, in practice so as to change the unsprung diameter of the stent ring. Couplings 22 made of a flexible material are however optimum for most applications.

Examples of material for the flexible couplings include: polyamide such as nylon, polyester, PTFE, cotton, other thread material including woven and braided steel. The flexible couplings could be tied to the sprung sections 10 but could also be molded thereto or otherwise bonded thereto.

The flexible couplings 22 are preferably inextensible or substantially inextensible, such that any compressive force applied to the structure will cause deformation of the sprung sections 10 in preference to stretching of the flexible couplings 22.

The flexible couplings preferably have a length sufficient to enable the stent ring to expand from 16 or 18 millimeters in diameter to 25 or 30 millimeters in diameter, in the case of aortic application, in another embodiment from a diameter of 8 millimeters to around 12 millimeters. The skilled person will appreciated that the actual length of the flexible couplings will be dependent upon the number and size of the sprung sections 10 and the intended diameters of the stent ring. These dimensions could also vary significantly form the indications given here; for instance it might be desired to have an iliac filter able to expand from 22 millimeters to around 47 millimeters.

Referring now to FIG. 2, there is shown the structure of FIG. 1 in what could be termed an overlapping arrangement, that is a configuration in which the adjacent arms 14, 16 of neighbouring sprung sections 10 overlap one another. Comparing FIGS. 1 and 2, in FIG. 1 neighbouring sprung sections are spaced from one another, whereas in FIG. 2 they partially overlap. In practice, the configurations could be described as circumferentially spaced and circumferentially overlapping. This overlap is achievable as a result of the flexible couplings 22 and in such a manner that there is no change in the configuration of the sprung sections 10 between these two states, that is the sprung sections 10 are not compressed or otherwise deformed. The flexible couplings 22 will not generate any effective restorative force.

Figure 3:
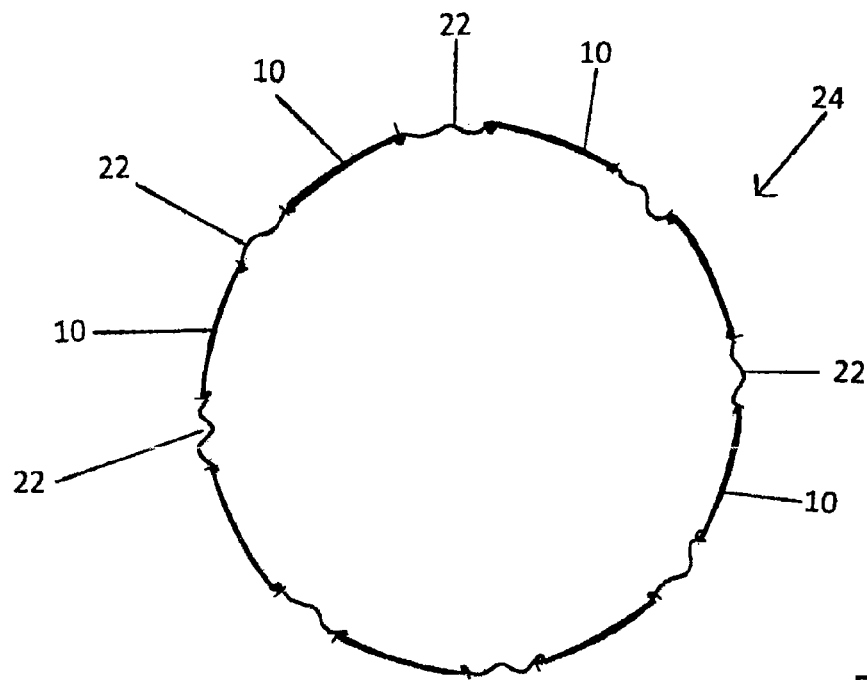
FIG. 3 is a plan view of the part of the stent structure of FIG. 1 at its greatest unbiased diameter.
Figure 4:
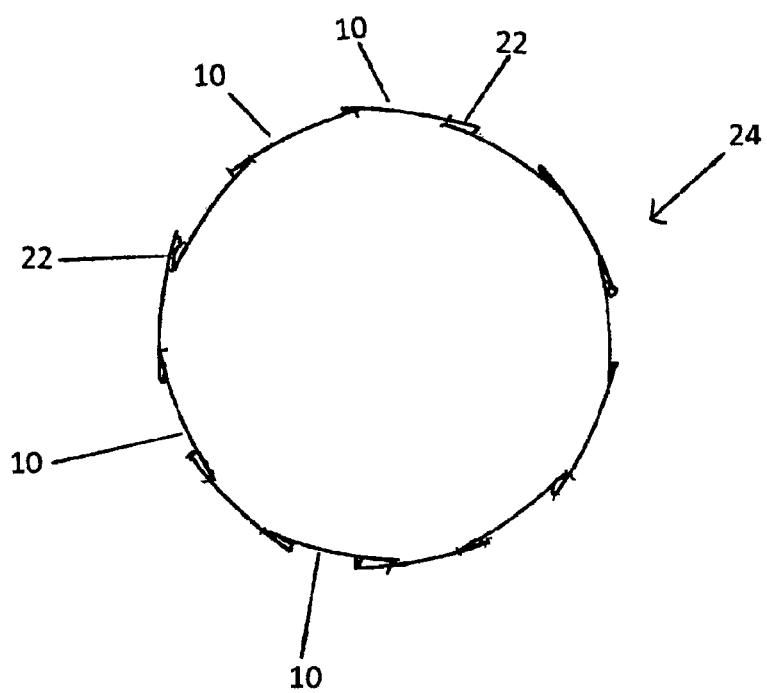
FIG. 4 is a perspective view of the stent structure of FIG. 2 in the smaller unbiased diameter.

Referring now to FIGS. 3 and 4, these show schematically a plan view of a stent ring 24 formed by the structure of FIG. 1 in these two configurations, that is with the sprung sections circumferentially spaced (FIG. 3) and circumferentially overlapping (FIG. 4). As can be seen, the stent ring 24 can have two different diameters with no deformation of the sprung sections 10. In practice, the stent ring 24 can have any diameter between the smaller and larger diameters depicted by FIGS. 3 and 4, especially with flexible couplings 22 made of flexible material such as thread, without any permanent deformation of the sprung sections 10.

It will be apparent in particular from a comparison of FIGS. 1 and 2, as well as a comparison of FIGS. 3 and 4, that the smaller and larger diameters of the stent 24 are achievable as a result of the flexible couplings 22, which enable neighbouring sprung sections 10 to move from the partially overlapped configuration of FIGS. 2 and 4 to the circumferentially spaced configuration shown in FIGS. 1 and 3. As a result of the flexibility of the couplings 22, there is no significant force required to change the stent ring 24 between these two configurations or, in practice, any configuration between the smaller and larger diameter configurations shown in these Figures. Advantages of this characteristic of the taught stent structure are described below in connection with FIG. 6.

It will be appreciated that when the flexible couplings 22 are made of thread or other flexible material, the couplings 22 can simply deform to allow the change in spacing between neighbouring sprung sections 10. With flexible couplings made of a substantially rigid element rotatably or pivotally coupled to the sprung sections, such movement will be by rotation of the flexible couplings.

Figure 5:
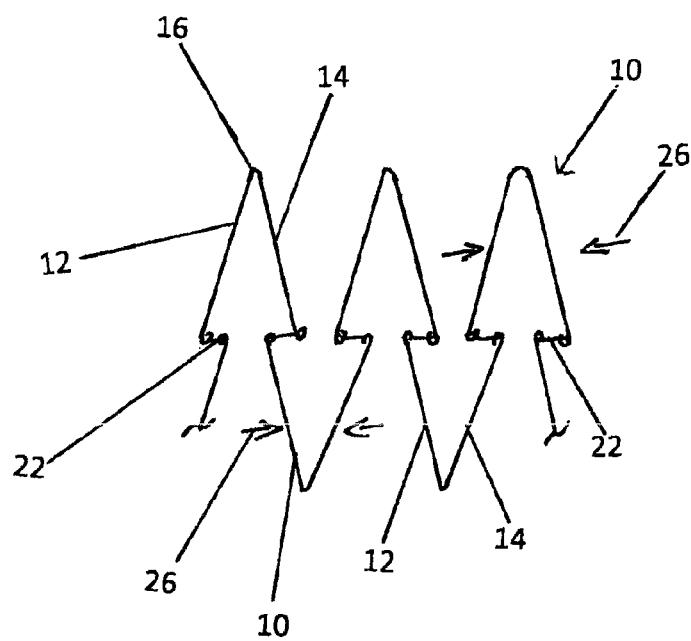
FIG. 5 is a plan view of the part of the stent structure of FIG. 1 as it would be in a radially compressed configuration.

Referring now to FIG. 5, the section of stent ring 24 shown in the Figure has the same configuration as in FIG. 2, that is which the neighbouring sprung sections 10 are in a partially overlapping arrangement, but in which the sprung sections 10 have been circumferentially compressed, in the direction of the arrows 26 in FIG. 5. This will occur, for example, when the stent ring 24 is compressed for delivery by an introducer assembly, in a manner known in the art. In this regard, the inextensibility of the flexible coupling elements 22 ensures that a compressive force applied to one of the sprung sections 10 will be imparted to the other sprung sections 10. This in practice has the effect of ensuring uniform circumferential and radial compression of a stent ring 24 and, similarly, substantially uniform expansion force produced by the structure when the sprung sections 10 are allowed to expand, typically within a patient's vessel. In the normal course of events it is preferable that the stent ring maintains an opening pressure on the vessel to secure fixation, until the stent ring has endothealised.

Considering FIG. 5 in connection also with FIGS. 4 and 3, when the sprung sections 10 are compressed in the manner shown in FIG. 5, the stent ring 24 will attain a diameter which is smaller than the diameter shown in FIG. 4 by virtue of the compression of the sprung elements 10. Generally, the stent ring 24 can be compressed at least as much as a conventional all metal stent ring.

From the compressed diameter to the smaller unsprung diameter 24 shown in FIG. 4, the stent ring 24 will impart a radial opening force by means of the stored spring energy of sprung elements 10. By contrast, from the smaller unbiased diameter shown in FIG. 4 to the larger diameter shown in FIG. 3, the stent ring 24 will exhibit no expanding force as the sprung sections 10 will have opened to their rest configurations at the smaller diameter shown in FIG. 4. Further expansion of the stent ring 24 occurs solely by the flexible couplings 22 in order to open out the structure, that is to separate circumferentially the sprung sections 10 from one another. Thus, expansion of the stent ring 24 is not limited and can follow the changes in the body.

Figure 6:
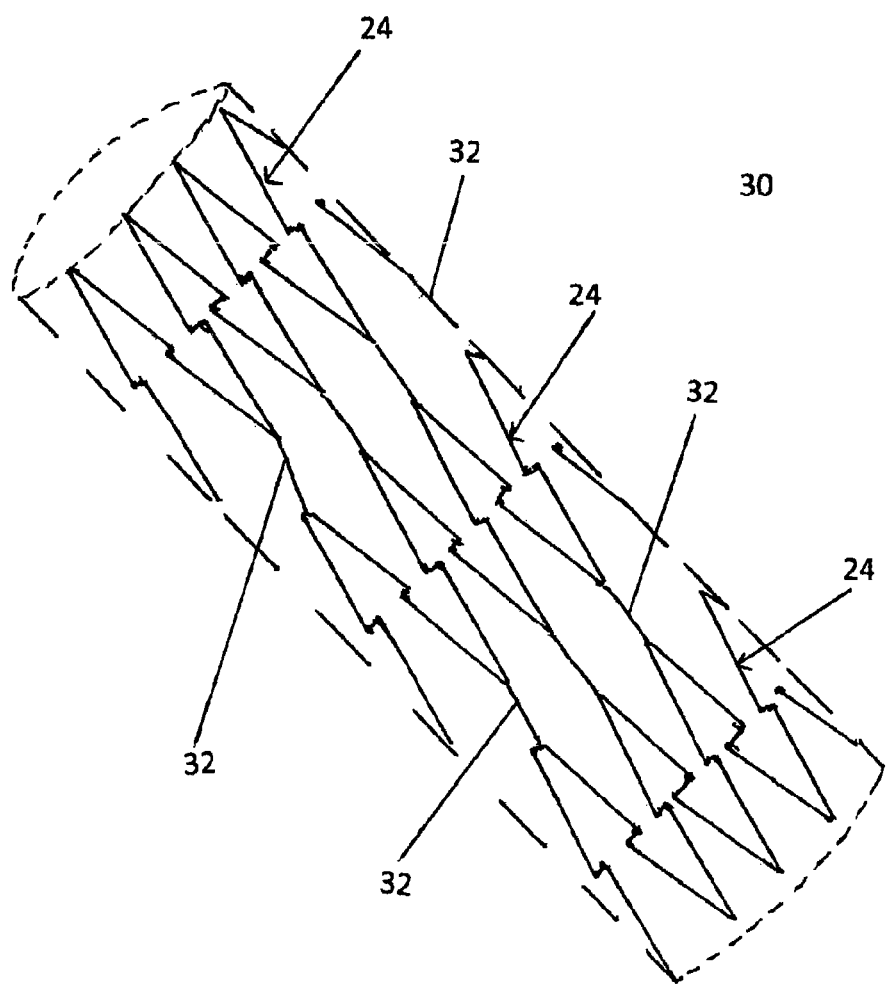
FIG. 6 is a perspective view of a stent including a plurality of the stent structures of FIG. 2 in the radially relaxed smaller diameter configuration.

Referring now to FIG. 6, there is shown in schematic form an example of stent 30 formed of a series of stent rings 24 arranged serially into a tubular structure. The stent rings 24 may be coupled to one another by tie bars 32, which may be relatively stiff tie elements made for example of a metal or metal alloy, but may equally be flexible tie elements similar to the flexible couplings 22, that is made of a flexible material such as thread or pivotable coupling. Flexible tie bars 32 give the stent 30 flexibility in the longitudinal direction.

The stent 30 shown in FIG. 6 could be used in place of a conventional all-metal or metal alloy stent used, for example, to keep a vessel open. Such a stent could be used, for example, to treat a collapsed or stenosed vessel or to reposition a dissection in a patient.

As with a conventional stent, the stent 30 is sized so as to apply a constant expansion force against the walls of a vessel within which it is placed. This expansion force has the effect of keeping the vessel open as well as retaining the stent reliability against the vessel wall with minimum chance of migration of the stent through the patient's vasculature. For this purpose, in some embodiments the stent sections 10 of the stent rings 24 may be provided with one or more barbs for anchoring purposes. Such barbs may be located only on an end most stent ring 24 and/or in other locations along the length of the stent 30, as deemed appropriate.

In the case of a vessel which remains substantially stable after implantation of the stent, the stent may remain in the vessel indefinitely. Over the course of time, particularly with an open stent structure of the type depicted in FIG. 6, the stent will become embedded within the walls of the vessel, typically by tissue ingrowth or endothealisation. In many circumstances, such endothealisation is not disadvantageous.

However, as explained above, there are medical circumstances in which the patient's vessel may change shape and/or size over the course of time. For example, when such a stent is implanted into a young patient, it can be expected that the patient's lumens will grow and thus increase in diameter over time. It is generally inadvisable to fit into the lumens of such a patient a stent which has a significantly greater unbiased diameter than the diameter of the lumen at the time of the medical procedure as so doing will impart a much greater expansion force on the lumen than is necessary, risking injury and trauma to the vessel wall. It is, on the other hand, disadvantageous to use a stent which is just right for the vessel at the time of commencement of treatment as that stent will then be too small later on in the life of the patient, with the result either that the stent will detach from the vessel wall with the risk of migration or that the stent, if it has endothealised will prevent natural growth of the vessel.

The stent structure shown in FIGS. 1 to 5 and described above and the stent 30 shown in FIG. 6 provide a solution to these difficulties. More particularly, the stent 30 can be radially compressed to fit within the lumen of a patient, in such a manner that the stent 30 will spring radially outwardly, to apply a constant and sufficient force against the vessel wall as required by the particular medical condition. This, as explained above, is achieved by the compression of the stent elements as depicted in FIG. 5 and described above. In this regard, the stent 30 is sized, that is chosen to have an uncompressed diameter in the configuration shown in FIG. 4, which is only slightly greater than the natural diameter of the lumen at the time of treatment, so as to impart a reasonable opening force and so as to maintain the stent 30 reliably in position in the lumen. Should the lumen then increase in size, for example as a result of growth of the patient, the stent 30 is able to expand in diameter by relative movement of the sprung sections 10 allowed for by the flexible couplings 22, from the configuration shown in FIG. 4 to that of FIG. 3. This is particularly advantageous when the stent 30 becomes endothealised into the vessel wall or is otherwise fixed to the vessel wall, for example by means of barbs and the like. This expansion of the stent structure 30 provides no resisting force, thus allowing the vessel to expand in normal manner. The stent 30, can therefore remain in place even in a growing patient, avoiding complications which can arise when attempting to remove the device from the patient.

The stent 30 is not limited to applications where the lumen may expand and otherwise change in shape, as it can equally be used for lumens which are expected to be substantially uniform in size over the course of time, for example as in an adult patient. The stent provides the advantage that once the lumen has recovered to its original size, any further unrestricted expansion of the stent 30, both along the entirety of its extent and also substantially individually from one part of the stent to another, allows free movement of the lumen as the patient moves, for example.

In the preferred embodiment, the flexible coupling elements 22 are made of a biodegradable material including SIS, polylactide and other known biodegradable materials. Biodegradable coupling elements 22 have the additional advantage of causing the stent 30, in particular the sprung elements 10 thereof, to become disconnected from one another after a given period of time. The flexible coupling elements 22 can be designed to degrade over the course of a number of weeks or months, for example, in order to cover the entire period over which a patient requires the functionality of the stent 30, with the result that the stent 30 after this period, by degradation of the coupling elements 22 and therefore of the disconnection of the sprung elements 24, will no longer impart an opening and/or straightening force to the vessel, thereby avoiding any long term unnatural forces being applied to the vessel wall. This can be particularly advantageous in situations where long term stent implantation may otherwise adversely affect the wellbeing of the vessel.

It is also envisaged that the sprung sections 10 could be attached to a graft tubing which may or may not be biodegradable. In such an embodiment, the sprung sections 10 may be longitudinally aligned along the graft tube and the graft tube infolded between radially adjacent sprung section 10 to provide functionality equivalent to that disclosed above. The sprung sections 10 could be directly coupled (tied or bonded for instance) to the graft material, thus requiring no separate couplings, although the latter option is not excluded from the scope of this disclosure.

In the preferred embodiment, as depicted in the drawings, it is preferred that the stent structure is uniform along the entire circumferential extent of each stent ring, that is that the entirety of the stent ring is formed of equal sprung sections 10 and equal flexible coupling elements 22. In other embodiments, only a part of the stent ring 24 may be connected by flexible coupling elements such that, for instance, a proportion of the stent ring 24 is made of interconnected V-shaped sprung sections (for instance in zigzag arrangement) and which are therefore permanently coupled to one another, with flexible couplings being located only in one or more arcs of the stent ring 24. This can provide a structure which produces a continuous force against the vessel wall across a part of the circumference of the vessel and yet allows opening of the structure at other circumferential regions of the vessel wall. The structure can be easily curved along a curved lumen and to move with the lumen, reducing the risk of fatigue fracture.

In other embodiments, the sprung sections 10 may have different sizes to one another.

The preferred shape of the sprung sections 10 is as shown in the drawings, that is in the form of V-shaped sections. Other embodiments, however, provide curved arms 12, 14 and also sprung sections which are more rounded, for example of a circular or sinusoidal shape.

It is to be understood that features of the different embodiments described above may be combined with one another as appropriate.

Although the claims are set out in single dependent form, it is to be understood that the features of the different claims may be combined with one another as if the claims were in multiple dependent format.

The invention claimed is:

1. A stent structure for an implantable medical device including a plurality of sections, a plurality of flexible couplings each disposed between adjacent sections so as to couple the plurality of sections together into an annular shape, wherein the plurality of sections store spring energy when compressed and the plurality of flexible couplings are substantially inextensible and do not produce any or only a nominal restoring force when deformed or reconfigured; said plurality of sections being radially compressible from a rest configuration; wherein said stent structure has a first diameter when the plurality of sections are compressed and a second diameter when the plurality of sections are in said rest configuration, said plurality of flexible couplings allowing for expansion of said stent structure to a third diameter greater than said second diameter.

2. A stent structure according to claim 1, wherein said plurality of flexible couplings are formed from a fibrous material.

3. A stent structure according to claim 2, wherein said plurality of flexible couplings are made from a thread.

4. A stent structure according to claim 1, wherein said plurality of flexible couplings are made of a biodegradable material.

5. A stent structure according to claim 1, wherein said plurality of sections are made of at least one of a polymer, a metal and a metal alloy.

6. A stent structure according to claim 5, wherein the plurality of sections are made of Nitinol.

7. A stent structure according to claim 1, wherein said plurality of sections are made of a shape memory material.

8. A stent structure according to claim 1, wherein said plurality of sections have a circumferentially curved or flat form.

9. A stent structure according to claim 1, wherein said plurality of sections are V-shaped.

10. A stent structure according to claim 1, wherein said plurality of sections are arranged in a zigzag configuration.

11. A stent structure according to claim 1, wherein said plurality of sections are each provided with at least one coupling element for attachment to at least one of the plurality of flexible couplings.

12. A stent structure according to claim 1, wherein said plurality of sections are made of a wire or are laser cut.

13. A stent structure according to claim 1, wherein each of the sections has two circumferentially spaced apart ends, wherein in an overlapping configuration one end is disposed between the ends of a first circumferentially adjacent section on one side of the section and the other end is disposed between the ends of a second circumferentially adjacent section on an opposite side of the section, and wherein in a spaced-apart configuration both ends are disposed between an adjacent end of the first circumferentially adjacent section and an adjacent end of the second circumferentially adjacent section.

14. A stent structure according to claim 13, wherein said plurality of flexible couplings are made from a thread, the thread allowing the stent structure to have any diameter between the second and third diameters without deforming the plurality of sections.

15. An implantable medical device including a plurality of the stent structure according to claim 1, wherein each of the plurality of the stent structures are coupled to at least one adjacent of the stent structures to form a tubular structure.

16. An implantable medical device according to claim 15, wherein the plurality of stent structures are coupled together by tie elements between longitudinally adjacent sections of adjacent stent structures.

17. An implantable medical device according to claim 16, wherein the tie elements are flexible.

18. An implantable medical device according to claim 17, wherein the tie elements are made of thread.

19. An implantable medical device according to claim 16, wherein the tie elements are biodegradable.

20. An implantable medical device according to claim 15, wherein the device is one of a stent, stent graft, vena cava filter and an occlusion device.

21. An implantable medical device including at least one stent ring formed of a plurality of sections and a plurality of flexible couplings each disposed between adjacent sections so as to couple the plurality of sections together into an annular shape, wherein the plurality of sections store spring energy when compressed and the plurality of flexible couplings are formed of substantially inextensible biodegradable thread and do not produce any or only a nominal restoring force when deformed or reconfigured; said plurality of sections being radially compressible from a rest configuration; wherein said stent ring has a first diameter when the plurality of sections are compressed and a second diameter when the plurality of sections are in said rest configuration, said plurality of flexible couplings allowing for expansion of said stent ring to a third diameter greater than said second diameter.

* * * * *